United States Patent [19]

Brown et al.

[11] 4,397,048

[45] Aug. 9, 1983

[54] REINFORCED PLASTICS ARTIFICIAL LIMB COMPONENT AND METHOD FOR MAKING SAME

[75] Inventors: Eric Brown, Wantage; Neil L. Hancox, Goosey, both of England

[73] Assignee: Chas. A. Blatchford & Sons Limited, Hampshire, England

[21] Appl. No.: 303,860

[22] Filed: Sep. 21, 1981

[30] Foreign Application Priority Data

Sep. 26, 1980 [GB] United Kingdom ............... 8031119

[51] Int. Cl.³ .................... A61F 1/08; B29C 17/06; B29C 27/26; B29D 3/02
[52] U.S. Cl. ................................. 3/2; 3/22; 264/258; 264/314
[58] Field of Search ............ 249/65; 3/1.9, 2, 8, 3/12, 21, 22; 128/80 R; 264/222, 257, 258, 314

[56] References Cited

U.S. PATENT DOCUMENTS

| | | | |
|---|---|---|---|
| 2,202,042 | 5/1940 | Blount | 264/314 |
| 2,485,827 | 10/1949 | Hartzell | 264/258 |
| 2,723,426 | 11/1955 | Pelley | 264/314 |
| 2,907,074 | 10/1959 | Rhodes | 264/314 |
| 3,520,002 | 7/1970 | Wellington | 264/222 |
| 3,823,208 | 7/1974 | Asbelle et al. | 264/222 |
| 3,902,944 | 2/1974 | Ashton et al. | 156/156 |

FOREIGN PATENT DOCUMENTS

| | | | |
|---|---|---|---|
| 2846504 | 4/1979 | Fed. Rep. of Germany | 3/21 |
| 53-34870 | 3/1978 | Japan | 264/314 |
| 1166604 | 10/1969 | United Kingdom . | |
| 1173762 | 12/1969 | United Kingdom . | |
| 1346660 | 2/1974 | United Kingdom . | |
| 1438184 | 6/1976 | United Kingdom . | |
| 1471547 | 4/1977 | United Kingdom . | |
| 1554353 | 10/1979 | United Kingdom . | |
| 1561435 | 2/1980 | United Kingdom . | |

OTHER PUBLICATIONS

Andersen et al., Orthopaedic Appliances Atlas, vol. 2, Edwards, Ann Arbor, Mich. (1960), pp. 267, 268, 269.
Klopsteg et al., Human Limbs and Their Substitutes, McGraw-Hill (1954), pp. 530, 713–718.
Williams et al., Implants in Surgery, (1973), pp. 89–94, Saunders, Phila.
Quigley et al., Atlas of Limb Prosthetics, Mosby, St. Louis, Jul. 1981, pp. 53–62.

*Primary Examiner*—Willard E. Hoag
*Attorney, Agent, or Firm*—Barnes & Thornburg

[57] ABSTRACT

An artificial limb component having one portion with an open channel cross-section and method for making the component in which woven sheets of carbon fibre reinforced plastics material in prepreg form are laid up on an inflatable expandable moulded mandrel, which is then placed in a lower mould half, a corresponding upper mould half being placed on the lower half to complete the mould. Air pressure is applied via pipe to the interior of the mandrel which is expanded within the mould halves to compress the prepreg sheets to the required shape.

11 Claims, 8 Drawing Figures

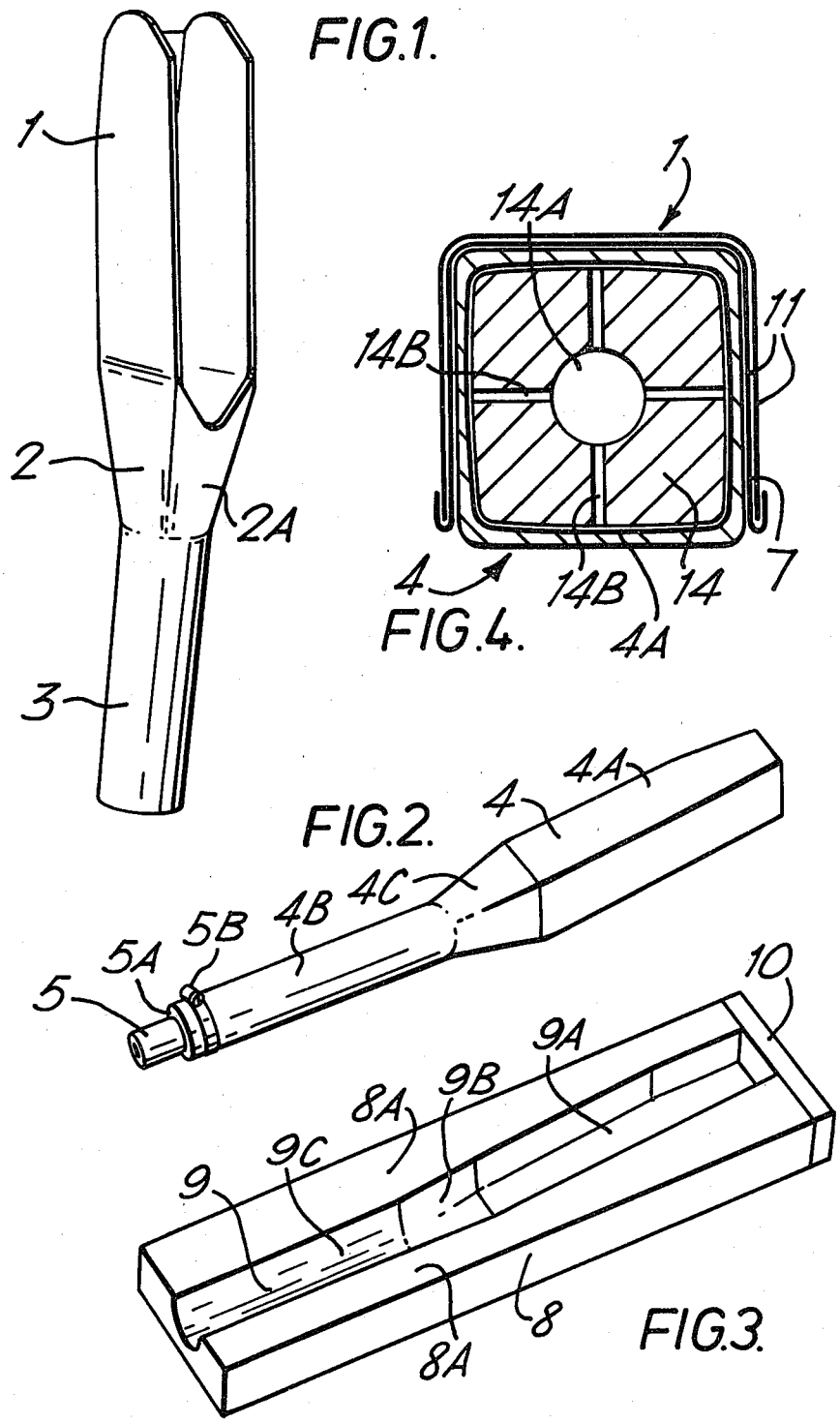

REINFORCED PLASTICS ARTIFICIAL LIMB COMPONENT AND METHOD FOR MAKING SAME

FIELD OF THE INVENTION

This invention relates to a method of making an artificial limb component, and in particular to a method of moulding a fibre reinforced plastics structural component of an artificial leg.

DESCRIPTION OF THE PRIOR ART

Fibre reinforced plastics materials are known as lightweight high strength materials from which a variety of moulded articles can be produced. Carbon fibre reinforced plastics material in particular is known for its relatively high strength-to-weight ratio. In one known method of producing a carbon fibre reinforced plastics moulding, resin impregnated bundles of carbon fibres are laid up in an open mould and are then heated and compressed by forcing a rigid mould-closing member onto the laid-up fibres and applying heat to the mould to cure the resin. This method has been widely used but is limited to the moulding of relatively simple shapes.

SUMMARY OF THE INVENTION

It is an object of this invention to provide a method of making a fibre reinforced plastics structural component having a relatively complex shape.

According to this invention there is provided a method of making a component of an artificial limb, the method comprising the steps of providing a plurality of sheets of plastics material, at least one of the sheets having reinforcement fibers running at a predetermined angle to reinforcement fibers of at least one other of the plurality of sheets, placing the sheets between an expandable internal mandrel and a rigid external mould, and expanding the mandrel to compress the composite material between the mandrel and the mould. Preferably the composite material is placed on the expandable mandrel so that when the mandrel is expanded the plurality of sheets is expanded and compressed between the mandrel and the mould. The mandrel is preferably a moulded silicone rubber element which is hollow so that it can be inflated inside the external mould. The reinforcement fibres are preferably carbon fibres.

The invention also includes a mould apparatus for making an artificial limb component, the mould comprising a rigid two-part external mould and an expandable internal mandrel, the inner surface of the external mould and the outer surfaces of the internal mandrel being shaped to co-operate in forming the component when a plurality of sheets of plastics material, each having reinforcement fibres is compressed between the mould and the mandrel by expansion of the mandrel. The invention also includes a component of an artificial limb whenever produced by the method of the invention.

The method of the invention can be used to produce a moulded fibre reinforced structural component having a partly enclosed interior space, for example a channel section or tubular section component. The use of an expandable mandrel allows such a structural component to be produced with a relatively complex internal shape.

The mandrel is preferably moulded in one piece and corresponds approximately to the internal shape of the structural component to be produced so that the composite material can be laid up on the surface of the mandrel in a required pattern and to a required thickness. The mandrel and the laid-up composite material are placed in one half of the external mould, which is then closed by fitting the other half of the external mould over the mandrel and composite material. This assembly can then be placed in a press which has means for heating the external mould for curing the resin of the composite material.

BRIEF DESCRIPTION OF THE DRAWINGS

The invention will now be described by way of example with reference to the drawings in which:

FIG. 1 is a perspective view of a structural component of an artificial leg shin produced by the method of the invention;

FIG. 2 is a perspective view of an expandable internal mandrel;

FIG. 3 is a perspective view of one half of a rigid external mould;

FIG. 4 is an enlarged transverse section through the mandrel with sheets of a composite material of fibres and resin laid up on three sides of the mandrel to form the channel section portion of the component of FIG. 1;

DESCRIPTION OF THE PREFERRED EMBODIMENT

Figure 5:
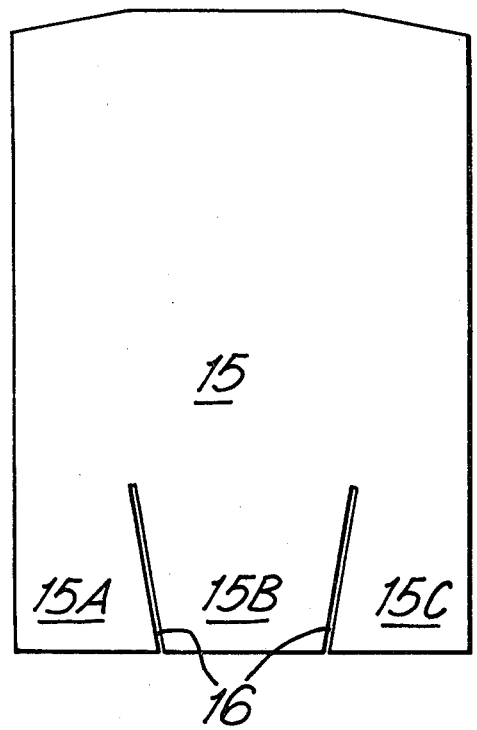
FIGS. 5, 6, and 7 are plan views of three different shapes of sheets of the composite material used in making the component of FIG. 1.

Referring to FIG. 1, an artificial leg shin component has an upper portion of three-sided channel section, a hollow transition portion 2, and a lower hollow portion 3 of circular cross-section. The top end of the upper portion 1 is shaped to house correspondingly shaped members of a knee chassis (not shown) which forms part of a knee joint mechanism. The open side of the upper portion 1 is at or near the rear face of the shin when it is part of an assembled artificial leg, and allows, for example, a swing control mechanism or knee lock to be positioned between the rear of the knee chassis and a pivot point just above the transition section 2. The lower portion 3 is shaped for attachment to a foot and ankle assembly.

The shin component is moulded in a resin impregnated carbon fibre composite material. The properties of this material are well-known, and its strength is such that a relatively thin wall thickness can be used so that the element is relatively light in weight. From FIG. 1 it will be apparent that there are two main changes in cross section from one end of the shin component to the other, that the portion 3 is of closed hollow cross section, and that the longitudinal axes of the portions 1 and 3 are at an angle relative to each other. The shin component is consequently of a relatively complex shape for a moulded fibre reinforced component and requires a more sophisticated moulding technique than is used for example when moulding a simple bar-shaped component.

The preferred method of making the shin component comprises, firstly, moulding a hollow, inflatably expandable, silicone rubber internal mandrel 4 to the shape shown in FIG. 2. This shape corresponds approximately to the required inner shape of the shin component 1. The mandrel 4 is expanded by supplying air under pressure by way of a pipe 5 fixed in the end 5A of the mandrel of a pipe clip 5B. It will be seen from FIG. 2 that the mandrel 4 has a portion 4A of generally square cross-section and a portion 4B of circular cross-section, these portions being joined by a transition portion 4C. Further the longitudinal axes of the portions 4A and 4B are at an angle to each other, corresponding to the angle between the axes of the portions 1 and 3 of the shin component. The right-hand end of the mandrel is closed.

FIG. 4 is an enlarged cross-section of the mandrel portion 4A and shows that the mandrel is hollow and contains a rigid core 14 over which the silicone rubber mandrel fits when not inflated, that is, in the non-expanded state. The core 14 has a central passage 14A to receive compressed air supplied through the pipe 5. The core also has a plurality of lateral branch passages 14B to distribute the air to the interior of the mandrel when it is to be expanded.

FIG. 3 shows a lower half 8 of a rigid external mould: the upper half is not shown, but would correspond to shape. The lower mould half 8 has parting surfaces 8A ad the upper mould half would have like surfaces. The mould halves are made of aluminium alloy and the inner surface 9 is polished. It will be understood that the inner surface 9 has portions 9A, 9B and 9C which correspond with the portions 1, 2 and 3 respectively of the shin component and with the portions 4A, 4C and 4B respectively of the mandrel 4. The length of the mould halves is such that when the mandrel 4 is enclosed in the mould, the pipe 5, mandrel end 5A and pipe clip 5B are outside the mould halves. Each mould half is closed at one end by a plate 10.

Figure 8:
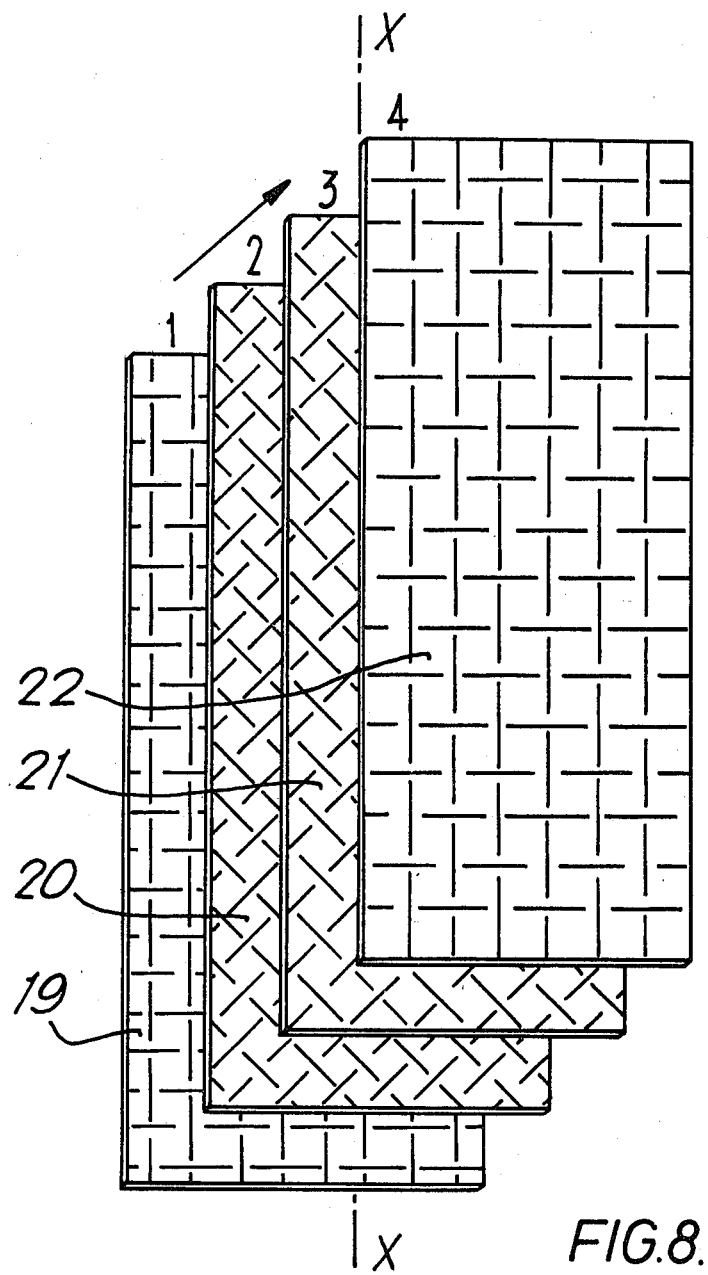
FIG. 8 is a diagram showing the sequence of laying sheets of the composite material on the expandable mandrel.

The shin component is formed of a number of sheets or layers of impregnated carbon fibre woven cloth 11 which are laid over the surface of the mandrel as diagrammatically shown in FIG. 4. The starting material is carbon fibre cloth pre-impregnated with an epoxy resin system, hereinafter referred to as "prepreg", having fibres running at right angles to each other, as will be described below with reference to FIG. 8. It is slightly tacky and its consistency is such that it will remain in position when laid up around the mandrel 4. Pieces of the prepreg sheets are cut out to a predetermined pattern, and then laid up around the mandrel 4.

Figure 6:
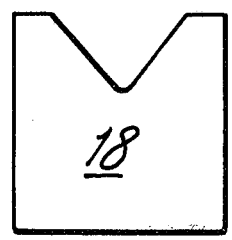
Figure 7:
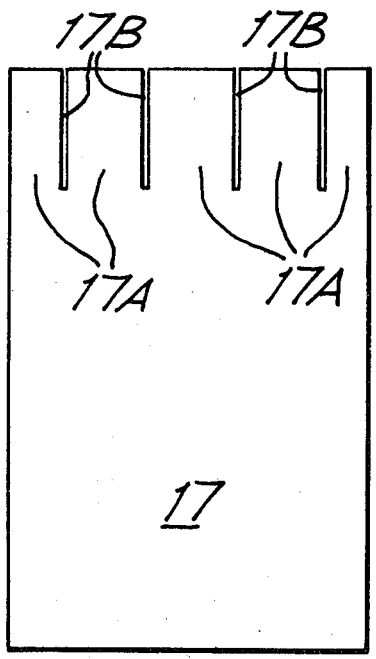

The sheet patterns are shown in FIGS. 5 to 7. The sheet 15 (FIG. 5) is shaped to fit over the three sides of the mandrel portion 4A, eventually to form (together with other sheets of the same pattern) the shin component upper portion 1. The sheet 15 has connecting or transition parts 15A, 15B and 15C separated by two slits 16. These parts 15A, 15B and 15C extend over and fit over the mandrel portion 4C. The sheet 17 (FIG. 7) is shaped to fit round the circular mandrel portion 4B, with connecting or transition parts 17A (formed by slits 17B) extending over the parts 15A, 15B and 15C on the mandrel portion 4C. The smaller sheet 18 (FIG. 6) is also placed on the mandrel portion 4C and in the final moulded component forms the part 2A of the portion 2, see FIG. 1.

Successive prepreg sheets are laid up on the mandrel 4 with the fibres in each sheet running at a predetermined angle to those of the previous layer. More specifically, and referring to FIG. 8, a first layer 19 may be laid up with the fibres running parallel and perpendicular i.e. at 0° and 90° relative to the longitudinal axis X—X of the portion 1, 2 or 3 in question, then the next layer 20 is laid up with the fibres running at +45° to the axis. This may be followed by another ±45° layer 21, and then another 0°, 90° layer 22, so that for example four layers of prepreg are used for all the parts of the shin component. The edges of each layer or sheet of prepreg are arranged to overlap adjacent layers or sheets, and successive layers or sheets are staggered with respect to one another to provide a relatively uniform distribution of discontinuities in the composite material.

In regions of potentially high stress, extra sheets of prepreg are preferably provided, for example in the transition portion 2. Eight or more layers may be used at that location. In the upper portion 1, which has two longitudinal edges, extra strength is provided by folding back one or more of the inner sheets 7 as shown in FIG. 4.

The laying up operation may be completed by laying an outer sheet or layer of a glass fibre reinforced composite material, which improves the resistance of the finished shin component to side impacts and enables any fractures in its structure to be more easily located. This latter advantage arises in that a fracture in a sheet of glass fibre reinforced composite material appears as a white line, whereas a like fracture would be almost invisible in the carbon fibre composite material.

The mandrel with the prepreg sheets on it is then placed in the one half 8 of the split external mould (FIG. 3). The other mould half is then fitted over the mandrel 4 and then the whole assembly is placed for example in a hydraulic press which has means for heating the platens of the press.

An air line (not shown) from a compressor is connected to the pipe 5, and then the platens of the press are heated to 150° C.; when the temperature of the mould reaches 70° C., an air pressure of 138 kPa is applied to the inflatable, expandable mandrel 4 via the pipe 5 and passages 14A, 14B to expand the mandrel 4, and also to expand the prepreg sheets or layers on it, so that they are compressed against the surfaces of the mould and the mandrel. The sheets or layers of composite material are cured during a period of 2 hours at 150° C. with pressure applied to the mandrel.

It will be seen that since the composite material is expanded outwards by the expansion of the mandrel 4, the diameter of the lower portion 3 increases from its diameter during the laying-up of the prepreg sheets. This largely avoids distortion of the prepreg sheets by puckering, as might occur if, for example, an alternative method were to be used, in which the prepreg sheets were compressed from the outside inwardly onto a rigid inner mandrel.

After curing, the mandrel 4 is de-pressurised and the shin component is removed from the mould. Since the mandrel 4 is flexible, the angled relationship between the two portions 1 and 3 of the shin component does not prevent removal of the mandrel.

Excess flash resin is removed from the shin component, which is then ready for assembly into an artificial leg.

I claim:

1. A lightweight, load-bearing shin component for an artificial leg, the component comprising an elongate upper portion of open channel shape in cross section, an elongate lower portion of closed tubular cross section, and an intermediate hollow portion joining the upper portion to the lower portion, the component being molded from a plurality of sheets of plastics material, at least two of the sheets having reinforcement fibers, the reinforcement fibers of at least one of the said at least two sheets running at a predetermined non-zero angle to reinforcement fibers of at least one other of the said at least two sheets said intermediate hollow portion being a transition portion between two portions of said component both having different configurations, in cross-section, from each other.

2. A component according to claim 1 wherein the upper portion is of rectangular three-sided open channel shape in cross section and the lower portion is of circular cross section.

3. A component according to claim 1 wherein the elongate upper and lower portions each has a longitudinal axis, the two longitudinal axes being disposed at an angle relative to each other.

4. A component according to claim 1 wherein the reinforcement fibers are carbon fibers.

5. A component according to claim 1 wherein the component has a length direction and wherein the said at least two sheets each has reinforcement fibers disposed at right angles in the sheet.

6. A component according to claim 1 wherein the component has a length direction and wherein fibers of one of the said two sheets are disposed parallel to the length direction and fibers of the other of the said two sheets are disposed diagonally to the length direction.

7. A method of molding a lightweight, load-bearing shin component for an artificial limb, the method comprising the steps of providing a plurality of sheets of plastics material, at least two of the sheets having reinforcement fibers, the reinforcement fibers of at least one of the said at least two sheets running at a predetermined angle to reinforcement fibers of at least one other of the said at least two sheets, placing the sheets between an expandable internal mandrel and a rigid external mold, and expanding the mandrel to compress the sheets between the mandrel and the mold, the mold including three differently shaped portions which cause the component to be formed with an elongated upper portion of open channel shape in cross section, an elongate lower portion of closed tubular cross section, and an intermediate hollow portion joining the upper portion to the lower portion where said component is to have an open channel shape, the open side being achieved by disposing said sheets on three sides of said mandrel only.

8. A method according to claim 7 wherein the sheets are placed on the expandable mandrel so that when the mandrel is expanded the sheets are expanded and compressed between the mandrel and the mold.

9. A method according to claim 7 wherein the mandrel is an inflatable hollow molded element.

10. A method accoding to claim 9 wherein the molded element is of silicone rubber.

11. A method according to claim 7 wherein the reinforcement fibers are carbon fibers.

* * * * *